(12) United States Patent
Giersch et al.

(10) Patent No.: US 9,668,798 B2
(45) Date of Patent: Jun. 6, 2017

(54) SONIC SCREW

(71) Applicants: Stryker European Holdings I, LLC, Kalamazoo, MI (US); Woodwelding AG, Stansstad (CH)

(72) Inventors: Helge Giersch, Laboe (DE); Klaus Dorawa, Schoenkirchen (DE); Philipp Seiler, Arboldswil (CH); Jörg Mayer, Niederlenz (CH)

(73) Assignees: Stryker European Holdings I, LLC, Kalamazoo, MI (US); Woodwelding AG (CH)

( * ) Notice: Subject to any disclaimer, the term of this patent is extended or adjusted under 35 U.S.C. 154(b) by 305 days.

(21) Appl. No.: 14/100,698

(22) Filed: Dec. 9, 2013

(65) Prior Publication Data

US 2014/0114362 A1  Apr. 24, 2014

Related U.S. Application Data

(63) Continuation of application No. 12/384,469, filed on Apr. 3, 2009, now abandoned.

(51) Int. Cl.
| | |
|---|---|
| *A61B 17/86* | (2006.01) |
| *A61B 17/88* | (2006.01) |
| *A61B 17/68* | (2006.01) |
| *A61B 17/70* | (2006.01) |
| A61B 17/74 | (2006.01) |

(52) U.S. Cl.
CPC .......... *A61B 17/8886* (2013.01); *A61B 17/68* (2013.01); *A61B 17/7098* (2013.01); *A61B 17/864* (2013.01); *A61B 17/742* (2013.01); *A61B 17/8822* (2013.01); *A61B 17/8875* (2013.01)

(58) Field of Classification Search
CPC .......................... A61B 17/862; A61B 17/864
See application file for complete search history.

(56) References Cited

U.S. PATENT DOCUMENTS

| | | | |
|---|---|---|---|
| 4,175,555 | A | 11/1979 | Herbert |
| 4,463,753 | A | 8/1984 | Gustilo |
| 4,653,489 | A | 3/1987 | Tronzo |
| 5,019,079 | A | 5/1991 | Ross |
| 5,171,279 | A | 12/1992 | Mathews |
| 5,375,956 | A | 12/1994 | Pennig |

(Continued)

FOREIGN PATENT DOCUMENTS

| | | |
|---|---|---|
| FR | 2909540 A1 | 6/2008 |
| JP | 9000539 A | 1/1997 |

(Continued)

*Primary Examiner* — Samuel Hanna
(74) *Attorney, Agent, or Firm* — Lerner, David, Littenberg, Krumholz & Mentlik, LLP

(57) ABSTRACT

A screw for fixation of, for example, a fracture having a hollow shaft, a first outer thread and radial openings at its distal end, and a second outer thread and an inner engagement portion at its proximal end. The second outer thread is adapted to engage with a tissue protection sleeve. The inner engagement portion is adapted to fit to a driving end of a driving tool. By way of this, forces in axial or radial direction may be applied to the screw by the sleeve, and forces in rotational direction may be applied by the driving tool. Therefore, the screw can be installed accurately at the intended site in an object.

2 Claims, 7 Drawing Sheets

(56) References Cited

U.S. PATENT DOCUMENTS

| | | | |
|---|---|---|---|
| 5,545,163 A * | 8/1996 | Miller | A61B 17/7007 606/287 |
| 5,868,749 A | 2/1999 | Reed | |
| 6,030,162 A | 2/2000 | Huebner | |
| 6,616,450 B2 | 9/2003 | Moessle et al. | |
| 7,037,309 B2 | 5/2006 | Weil et al. | |
| 7,335,205 B2 | 2/2008 | Aeschlimann et al. | |
| 7,354,442 B2 | 4/2008 | Sasso et al. | |
| 7,699,852 B2 | 4/2010 | Frankel et al. | |
| 8,025,677 B2 | 9/2011 | Freid | |
| 8,216,243 B2 | 7/2012 | Yevmenenko et al. | |
| 8,273,109 B2 | 9/2012 | Jackson | |
| 8,273,113 B2 | 9/2012 | Frenk et al. | |
| 2003/0125744 A1 | 7/2003 | Contiliano et al. | |
| 2004/0030341 A1 | 2/2004 | Aeschlimann et al. | |
| 2004/0138662 A1 | 7/2004 | Landry et al. | |
| 2004/0162560 A1 | 8/2004 | Raynor et al. | |
| 2004/0225292 A1 * | 11/2004 | Sasso | A61B 17/8615 606/916 |
| 2004/0267265 A1 | 12/2004 | Kyle | |
| 2005/0010224 A1 | 1/2005 | Watkins et al. | |
| 2005/0107800 A1 | 5/2005 | Frankel et al. | |
| 2005/0113929 A1 | 5/2005 | Cragg et al. | |
| 2006/0025773 A1 * | 2/2006 | Yevmenenko | A61B 17/863 606/916 |
| 2006/0247642 A1 | 11/2006 | Stone et al. | |
| 2008/0109007 A1 | 5/2008 | Schwager et al. | |
| 2008/0147128 A1 * | 6/2008 | Fritzinger | A61B 17/862 606/304 |
| 2008/0262517 A1 * | 10/2008 | Wieland | A61B 17/00491 606/151 |
| 2009/0018471 A1 | 1/2009 | Dorawa et al. | |
| 2009/0018590 A1 * | 1/2009 | Dorawa | A61B 17/864 606/301 |
| 2009/0275994 A1 * | 11/2009 | Phan | A61B 17/7064 606/86 A |
| 2010/0211074 A1 | 8/2010 | Hansson et al. | |

FOREIGN PATENT DOCUMENTS

| | | |
|---|---|---|
| SU | 827050 | 5/1981 |
| WO | 2009014485 A1 | 1/2009 |

* cited by examiner

SONIC SCREW

CROSS-REFERENCE TO RELATED APPLICATIONS

The present application is a continuation of U.S. patent application Ser. No. 12/384,469, filed Apr. 3, 2009, the disclosure of which is incorporated herein by reference.

BACKGROUND OF THE INVENTION

The invention relates in general to sonic fusion technology. It relates more particularly to a screw and a method for the fixation of fractures, particularly bone fractures. The invention relates to a screw for augmenting within a fractured object, to a system including tools to implement the screw into the fractured object, as well as to the use of the mentioned system. The fractured object might be a bone or a wooden or plastic object like furniture.

Known from U.S. Pat. No. 4,653,489 is a system wherein a fixation cement is introduced through a screw into a portion of a bone afflicted by osteoporosis. Femoral neck fractures as well as distal femoral fractures can be fixated by means of this device.

The system in accordance with prior art comprises a screw having a flow cavity, i.e. an axial through bore screw through with bone cement can be introduced into the portion at the tip of the screw. The bone cement is advanced by a device which is releasably attached to the subsequent end of the screw. This device is similar to commercially available syringe, in comprising substantially a cylindrical barrel and a plunger. The barrel forms a cavity in which the plunger is moveable backwards and forwards.

In use of this prior art device, the fixation cement is filled into the barrel, after which the plunger is urged against the cement. By applying manual compression force, the fixation cement is jetted into the axial through bore of the screw. Due to the pressure, the fixation cement is adequately fluidized, so that it can pass through the proximal end of the screw into the bone, as a result of which the screw is augmented in the bone.

This system has the drawback that the manual pressure applied to the fixation cement varies, not only basically from application to application, but also during the application itself, so that the distribution of the fixation cement within the portion of the bone at the tip of the screw is neither reliable nor even.

A device for fixing bone fractures is shown in U.S. Patent Application Publication No. 2009/0018590 the disclosure of which is incorporated herein by reference. A device for applying ultrasonic energy to a screw is shown in U.S. Patent Application Publication No. 2009/0018471 the disclosure of which is incorporated herein by reference. As shown in FIG. 27 of U.S. Pat. No. 7,335,205, use of ultrasonic energy and a polymer pin is known in fracture fixation. The disclosure of U.S. Pat. No. 7,335,205 is incorporated herein by reference.

BRIEF SUMMARY OF THE INVENTION

One aspect of the invention may be to provide a screw and a method by means of which a reliable and even augmentation of the screw in an installation site in an object can be assured.

Generally, a screw for fixation of a fracture comprises a shaft having a distal end, a proximal end and a central axis, a through bore extending along the central axis of the shaft, a first outer thread and a radial opening located at the distal end (furthest from the user), and a second outer thread as well as an inner tool engagement portion located at the proximal end (closest to the user) of the shaft.

The screw may have a shaft which is substantially a hollow and elongated element, wherein the axial through bore is formed along the central axis so that the thickness of the wall of the shaft is constant in circumferential direction. Preferably, the shaft will have a round cross section.

At the distal end (the tip portion or leading end of the screw), the first outer thread is capable of cutting into bone (or wood). Therefore, the first outer thread extends along the first few centimeters of the length of the shaft, starting at the tip of the screw in the direction towards the proximal end. According to an exemplary embodiment, the first outer thread might be tapered at the tip of the screw to allow a better introduction of the screw into an object of interest like a bone or a wooden object (for example furniture).

From the central through bore through the wall of the shaft in the portion of the first outer thread, there is formed at least one opening in radial direction. Providing the tip portion of the screw with a few openings may allow for a better distribution of a suitable material used for augmenting the screw in an object of interest.

At the other end, the proximal end of the screw, there may be formed a second outer thread, which extends preferably only a few millimeters along the axis of the shaft. This second outer thread is another kind of a thread compared with the first outer thread, since the second outer thread is adapted to engage with a tissue protection sleeve. To avoid negative interdependencies like irritations or lesions, between the second outer thread and tissue surrounding the bone, the outer contour of the windings are flattened or rounded so as to have a smooth contact area.

According to a further embodiment, the second outer thread might be adapted to be connected to an augmentation tool, wherein, for example, the housing of the augmentation tool is supported at the proximal end of the screw by means of the second outer thread, and a sonotrode capable of transmitting ultrasound vibrations is in contact with a polymer pin located inside the screw.

Furthermore, the proximal end of the screw includes an inner tool engagement portion. This means that the screw might be coupled with a driver having a corresponding driving end. This driving end may be hexagonal or a TORX® drive, wherein the driver may also be a wrench. It is noted that the driver may also be driven by a power source including an electric, pneumatic or other suitable mechanism.

According to a further embodiment, the outer diameter of the second thread is greater than an outer diameter of the shaft. Therefore, a step will be formed between the outer thread at the proximal end and the shaft. According to that embodiment, the screw further comprises a collar between the second outer thread and the shaft to provide a smooth junction or shoulder between the outer thread and the shaft. For example, the collar may be formed as a part-spherical head portion with the spherical surface facing the distal end of the screw.

For the case of an implantation of a screw into a bone, a set or system for installation of the screw according to the invention comprises, beside the screw as described above, a driving tool adapted to engage with the inner tool engagement portion of the screw, and a hollow tissue protection sleeve adapted to engage with the second outer thread of the screw.

The tissue protection sleeve is a kind of a lengthening piece, which may be suitable to facilitate the introduction of the screw into a bone, wherein muscles or other tissue surrounding the bone will complicate the attachment of an augmentation tool directly at the proximal end of the screw.

With two separate elements, i.e. the sleeve and the driver, each engaging directly at the proximal end of the screw, it is possible to apply forces with different direction precisely onto the screw, so that the screw may be positioned accurately at a appropriate site. With the driver, forces in circumferential direction may be applied to screw in (or out for explanation) the screw. With the sleeve, force in axial or radial direction may be applied to the screw. As another advantage, the screw may be held in place by the screw driver while the tissue protection sleeve is loosened and removed from the proximal end of the screw.

It will be understood that the combination of connections at the proximal end of the screw, i.e., the outer thread for a connection with a sleeve and the inner engagement portion for a connection with a driving tool, may also be suitable to manipulate a nail, a drive screw or another implant. Therefore, all aspects described with respect to a screw may also apply to a nail, a drive screw or other kind of implant.

According to a further embodiment, the set further comprises a polymer pin made of a fluidizable material, adapted to be inserted into the through bore of the screw, and an augmentation tool including a sonotrode for fluidizing the polymer material of the polymer pin, wherein the augmentation tool is adapted to be coupled with the proximal end of the screw or the proximal end of the tissue protection sleeve, wherein the sleeve may be located between the screw and the augmentation tool.

It is noted, that the material of the polymer pin may be bio-compatible, wherein a bio-compatible material may be a material which does not negatively interfere with human or animal tissue.

Examples of bio-compatible and also fluidizable materials may be specially adapted metal alloys such as titanium or specific plastics, e.g. PEEK (Polyetheretherketone), UHM-WPE (Ultra high molecular weight polyethylene), PLA (Polylactic acid), PLLA (Poly-L-lactide), PLDLA (Poly(D, L-Lactid)), PDLLA (Poly-DL-lactide), PVDF (Polyvinylidene Difluoride).

Furthermore, it may be advantageous, that the material of the polymer pin is bio-absorbable. One possible bio-absorbable material comprises a copolymer comprising between 50% and 90% Poly-L-lactide and between 10% and 50% Poly-D, L-lactide. In particular, the bio-absorbable material may be a copolymer comprising 70 weight % Poly-L-lactide and 30 weigh % Poly-D, L-lactide. Preferably, the bio-absorbable material may be formed as an amorphous material.

It may be understood that in a set including a tissue protection sleeve, the length of the sonotrode of the augmentation tool as well as the length of the screw driving tool correspond in length and allow both to be used in conjunction with a tissue protection sleeve mounted on the screw.

In use, the tissue protection sleeve will be coupled with the proximal end of the screw, the driving end of the screw driver will be connected with the inner tool engagement portion at the proximal end of the screw, while the shaft of the screw driver is at least partially located inside the tissue protection sleeve. Now, the screw might be introduced or located in the object of interest, i.e. the screw may be screwed into the bone.

After positioning of the screw, the screw driver will be disconnected from the screw, the polymer pin will be inserted through the tissue protection sleeve into the through bore of the screw, and an augmentation tool may be coupled with the proximal end of the tissue protection sleeve, wherein the sonotrode of the augmentation tool is located inside the tissue protection sleeve as well as inside the screw shaft, and is in contact with the polymer pin inside the screw. Subsequently, by applying ultrasound energy and/or force to the polymer material of the polymer pin, the polymer material will be fluidized or melted such that the material may flow out of the openings at the distal end of the screw into the cavities of the bone (or the wood).

The ultrasonic sonotrode may be adapted to generate ultrasonic vibrations at the tip with a frequency of between and 50 kHz, preferably between 20 and 30 kHz, and a suitable vibration amplitude may be in the range between 1 and 100 µm, preferably between 5 and 30 µm. The vibrations can be generated preferably in a direction along the vibration shaft and/or in a direction perpendicular to the vibration shaft.

Additionally, a certain pressure should be applied by way of the sonotrode to the polymer pin. Firstly, the pressure will ensure that the vibrations will be transmitted reliably from the sonotrode to the polymer pin. Secondly, the pressure will push the melted material of the pin out of the screw.

A description in more detail of the steps performed while using the set or system for installation of the screw according to the invention may be followed in conjunction with the detailed description of an exemplary embodiment below.

It has to be noted that embodiments of the invention are described with reference to different subject matters. In particular, some embodiments are described with reference to the methods used, whereas other embodiments are described with reference to the apparatus used, however, a person skilled in the art will gather from the above and the following description that, unless, otherwise notified, in addition to any combination of features belonging to one type of subject matter, also any combination of features relating to different subject matters is considered to be disclosed with this application.

The aspects defined above and further aspects, features and advantages of the present invention can also be derived from the examples of the embodiments to be described hereinafter and are explained with reference to examples of embodiments to which the invention is not limited.

BRIEF DESCRIPTION OF THE DRAWINGS

The invention will now be detailed by way of an exemplary embodiment with reference to the attached drawings.

It is noted that the illustration in the drawings is only schematically and not to scale. In different figures, similar elements are provided with the same reference signs.

DETAILED DESCRIPTION

FIGS. 1 to 6 are a schematic illustration showing different steps in the use of a set of devices for installation of a screw according to the invention.

Figure 1:
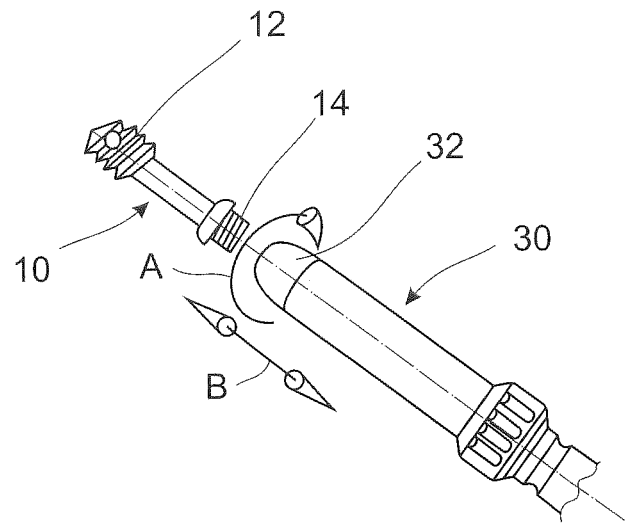
FIGS. 1 to 6 show subsequent steps illustrating the use of a set of devices for installation of a screw according to the invention.

FIG. 1 shows a screw 10 including a first outer thread 12 and a second outer thread 14. A tissue protection sleeve 30 is shown with a small distance behind the second outer thread 14 of screw 10. Furthermore, there is indicated by arrow A that the tissue protection sleeve may be screwed onto the second outer thread 14. Even though the arrow A indicates a right hand thread, a left hand thread may also suitable.

Consequently, a distal end 32 of tissue protection sleeve 30 is provided with an inner thread corresponding to outer thread 14 of screw 10. The arrow B indicates that a force transmission from the tissue protection sleeve to the screw is possible in axial direction.

Figure 2:
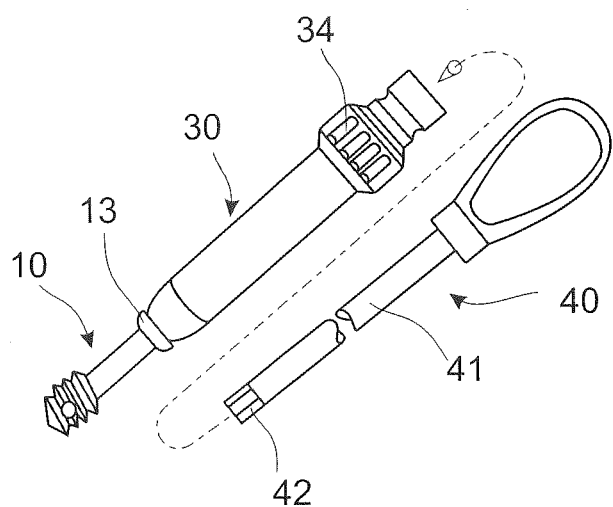

With the tissue protection sleeve 30 connected with the screw, it may be possible to insert a shaft 41 of a screw driver 40 in the tissue protection sleeve 30 so as to bring an engagement portion 42 of screw driver 40 into engagement with the inner engagement portion of screw 10. Furthermore illustrated in FIG. 2 is the configuration of screw 10 at the connection point with the tissue protection sleeve 30. Screw 10 includes a collar 13 near to the second outer thread at the proximal end of the shaft. The tissue protection sleeve 30 is slightly conical at the distal end 32 of the sleeve 30. Therefore, the junction between screw 10 and tissue protection sleeve 30 may be smooth, which will provide for less tissue irritation.

Figure 3:
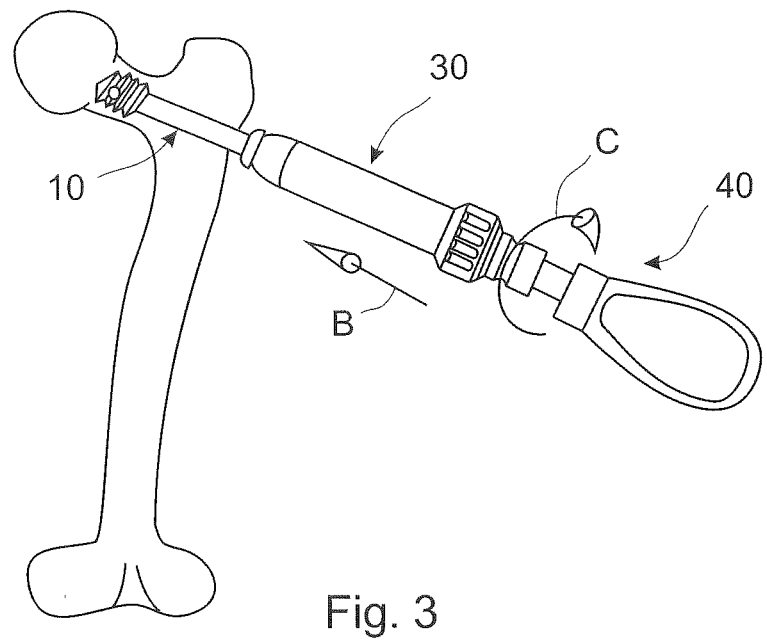

FIG. 3 shows that by means of the assembly consisting of screw 10, tissue protection sleeve 30 and screw driver 40 it is possible to insert or implant the screw 10 into a bone at a fracture site. In this example, the screw is implanted into a femoral bone to fix a fracture of the femoral neck. Indicated by the arrows B and C is the possibility to simultaneously press in axial direction and rotate around the axis of the screw so as to easily drive screw 10 into the bone.

Figure 4:
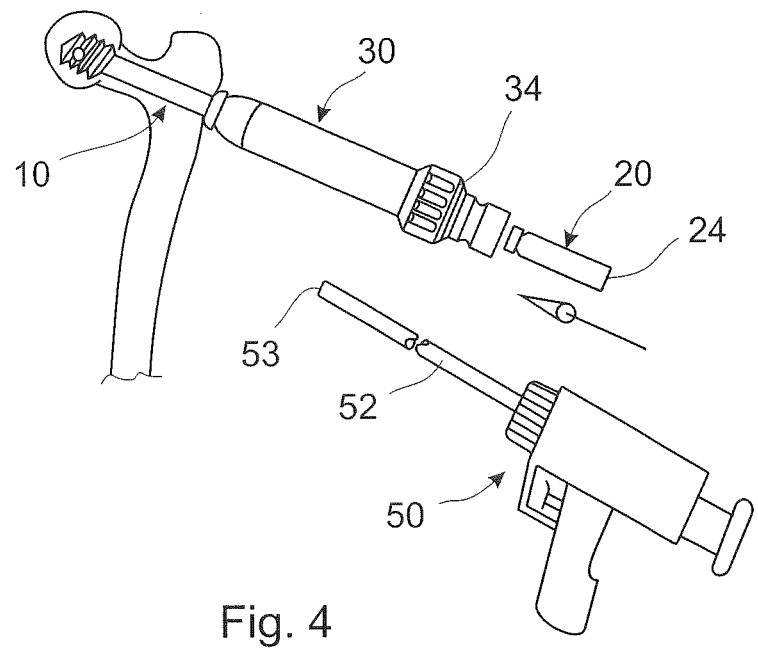

In FIG. 4 there is shown a state in which screw 10 is already inserted into the bone and the screw driver is removed from screw 10 and out of the tissue protection sleeve 30. Now, as depicted in FIG. 4, a polymer pin 20 may be inserted into screw 10 through tissue protection sleeve 30. Furthermore, there is shown an augmentation tool 50 including a sonotrode 52 with a tip 53. The length of the sonotrode 52 is dimensioned so that when the polymer pin is inserted into screw 10 tip 53 of sonotrode 52 will make contact with a proximal end 24 of the polymer pin 20 inside screw 10 while the housing of augmentation tool 50 is coupled with proximal end 34 of tissue protection sleeve 30.

Figure 5:
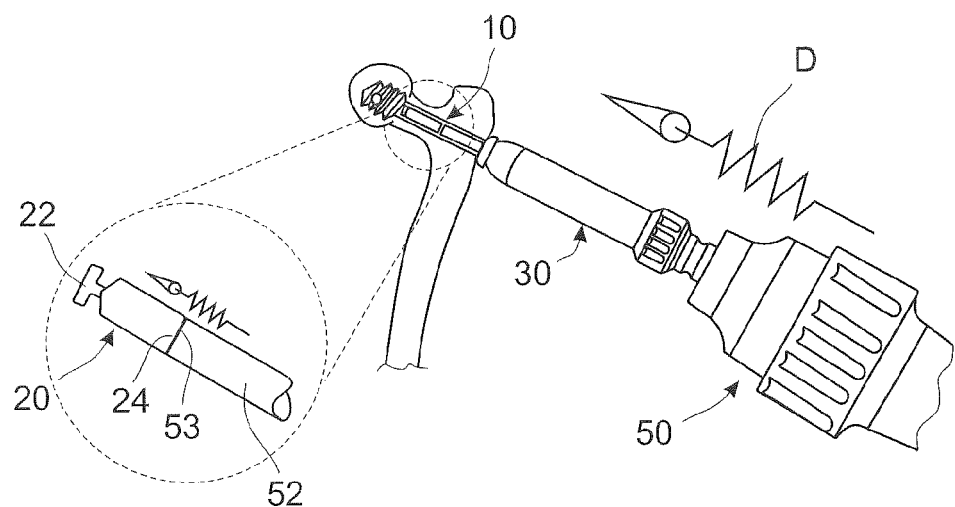

The assembly of screw 10, tissue protection sleeve and augmentation tool 50 is also depicted in FIG. 5. Furthermore, in FIG. 5 screw 10 is illustrated as a section view so that polymer pin 20 as well as sonotrode 52 is visible inside screw 10. In an additional detailed view, there is shown polymer pin 20 together with an insert 22 at the tip of the polymer pin, wherein the insert 22 provides for a support inside screw 10, when, by means of sonotrode 52 an ultrasonic vibration as well as an axial force is applied to the polymer pin. The ultrasonic vibration and the axial force are indicated by arrow D in FIG. 5.

To provide a appropriate support for insert 22 at the distal end of polymer pin 20 there is formed a step in the inner wall of the through bore of the screw near the distal end of the through bore.

It is noted that the counter force to the force applied in axial direction from the sonotrode to the polymer pin, will be a pull force affecting on the tissue protection sleeve and thus on the second outer thread of the screw and the connection between the sleeve and the housing of the augmentation tool.

Figure 6:
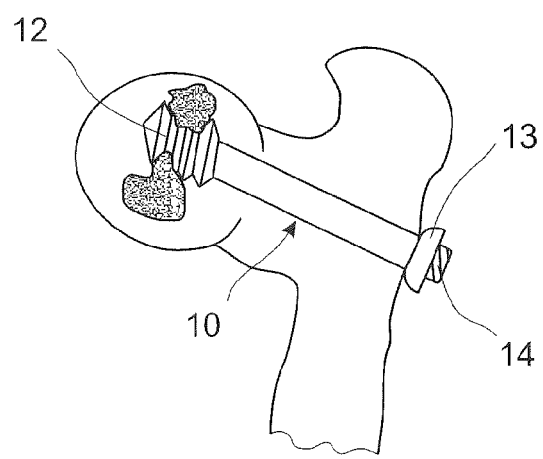

By applying the energy and/or force to the polymer pin, the material of the polymer pin will melt or fluidize so that the melted polymer material will exit out of the tip portion of the screw 10 through radial openings into the bone. Accordingly, FIG. 6 shows a situation in which the screw 10 is inserted into the bone, the tip of the screw 10 is augmented by the polymer material and the augmentation tool as well as the tissue protection sleeve is already removed from the proximal end of the screw.

Figure 7:
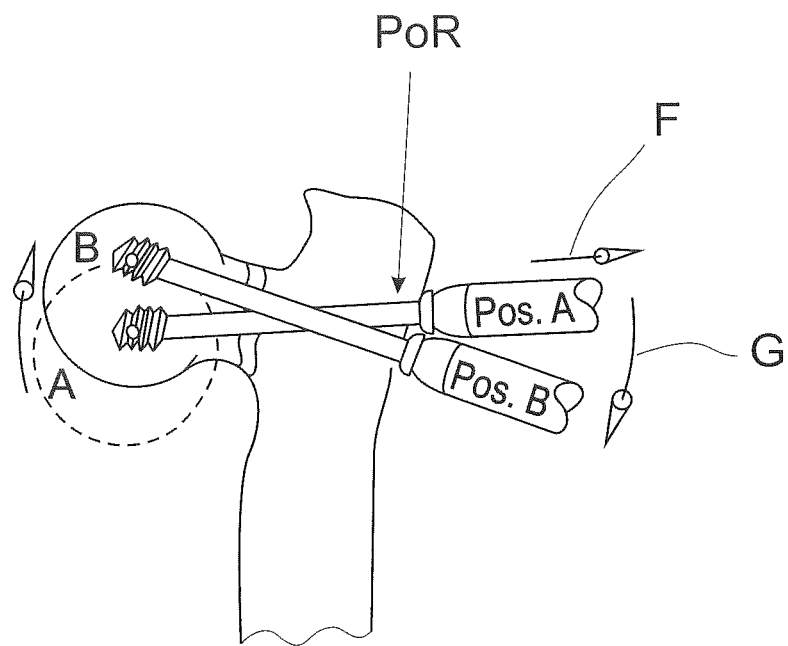
FIG. 7 illustrates a possible adjusting of fractured pieces relative to each other.
Figure 8A:
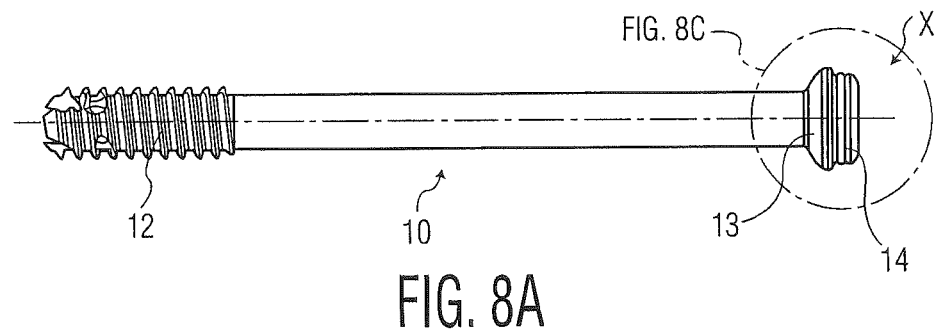
FIG. 8A is a side view of the screw of the present invention.
Figure 8B:
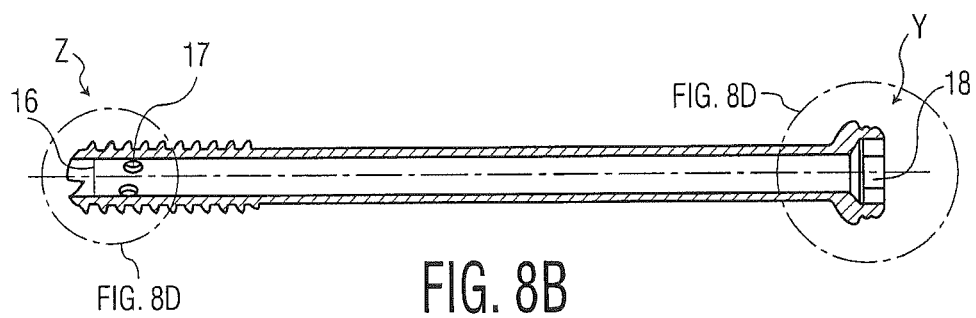
FIG. 8B is a cross-sectional view of the screw of FIG. 8A.
Figure 8C:
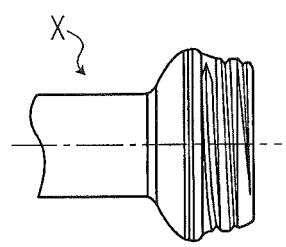
FIG. 8C is an enlarged view of the head portion indicated as X in FIG. 8A and FIG. 8D portions "Y" & and "Z" are an enlarged cross-sectional views of the ends of the cross-sectional view of FIG. 8B designated as Y and Z.
Figure 8D:
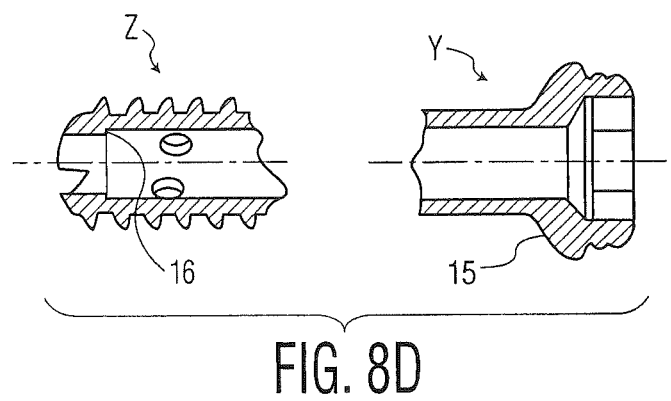

FIG. 7 illustrates another possibility during the implantation of the screw, i.e. the fixation of a fracture of a femoral neck. After the screwing in of the screw into the bone, it may be possible especially in an osteoporotic bone to pivot the screw at the entrance into the bone in the corticalis so as to correctly position the joint head of the femur relative to the neck and shaft of the femur (for example from Position A to Position B). PoR in FIG. 7 indicates the point of rotation. Such a correction or movement is possible as long as the tissue protection sleeve is connected to the proximal end of the screw, since said sleeve may be gripped and a force for a pivot movement (indicated by arrow G) as well as a pull movement (indicated by arrow F) may be performed.

FIG. 8 is an illustration of a screw according to one embodiment of the invention. The illustration includes a side view, a section view and the proximal end of the screw as detail side view and detail section view.

As shown in FIG. 8, a screw 10 according to the invention may comprise at its distal end an outer thread 12, radial openings 17 and a step 16 in the axial through bore. The outer thread 12 may be machined only in an end portion of the shank, wherein the thread may also cover the shank of the screw full length. Provided along the longitudinal center line of the screw is a through bore composed of two bore portions. The proximal bore portion comprises a first diameter and the distal bore portion a second diameter, wherein the first diameter being larger than the second diameter. The proximal bore portion may form the main portion of the through bore. Just a small end portion of the shank of the screw in which portion thread 12 is machined is formed by the distal bore portion. The transition from the proximal bore portion to the distal bore portion is formed by step 16 in the diameter. Step 16 in the diameter forms an annular ridge having substantially right-angled edges at the wall of the through bore within the screw. Each edge of step 16 in the diameter may be machined flat or rounded or conical. However, the step may also provide for a closed distal end of the screw.

In addition, the screw 10 features openings or holes 17 radially configured through the wall of the screw. Openings may be configured in differing directions, for example perpendicular to the longitudinal centre line of the screw and arranged in the end portion with thread 12. Preferably openings 17 are arranged in a region of the end portion which also features the proximal bore portion. According to one embodiment two openings 17 may be configured axially juxtaposed in the proximal bore portion and through thread 12. Furthermore, four such pairs of openings may be evenly distributed about the circumference of the screw, in other words, circumferentially spaced by 90°. It is, however, just as possible that three, four, five or more openings may be provided circumferentially and it is not necessary that the holes circumferentially distributed are all at same level. The openings might also be distributed circumferentially along the thread turn. Apart from this, transverse or longitudinal oblong holes, slots, or the like may be provided.

Furthermore the position of step 16 in diameter together with the openings 17 in the wall can be positioned optionally along the longitudinal centre line and thus the siting of the augmentation can be determined in accordance with the particular application and the desired effect.

As also shown in FIGS. 8A to 8D, the screw comprises at its proximal end a collar 13 forming a shoulder or transition from the outer diameter of the shaft to an outer diameter of a second outer thread 14. The collar 13 has a part-spherical surface 15 facing the distal end of the screw 10. As mentioned above, the outer thread 14 is machined such that the outer edges of the thread line are rounded or at least not sharp. Since the proximal end of the screw i.e. the collar 13 and the outer thread 14 will remain outside of a bone into which the screw is implanted, these elements should be formed such that an irritation of or insurance to the tissue surrounding the end of the screw can be avoided. The length of the outer thread may be only a few millimeters, just enough to ensure a reliable connection between the screw and a tissue protection sleeve. The forces in axial and/or in radial direction may be transmitted through this threaded connection. Furthermore, the end projecting out of the bone should be as short as possible.

Further, the screw comprises an inner tool engagement portion 18 in its proximal end portion. The inner engagement portion 18 is provided for transmission of rotational forces. Furthermore, by holding the screw by means of a screw driver engaged in the inner engagement portion tissue protection sleeve 30 may be easily removed from the outer thread of the screw. The shape of the inner engagement portion may be a torx or hex fitting to a corresponding driving end of a screw driver. However, said shape may also be any suitable driving connection including slot, cross, customized or else. The only restriction is the fact that the axial through bore in the screw will provide for absence of material in the center portion of the inner engagement portion.

Figures 9, 9A:
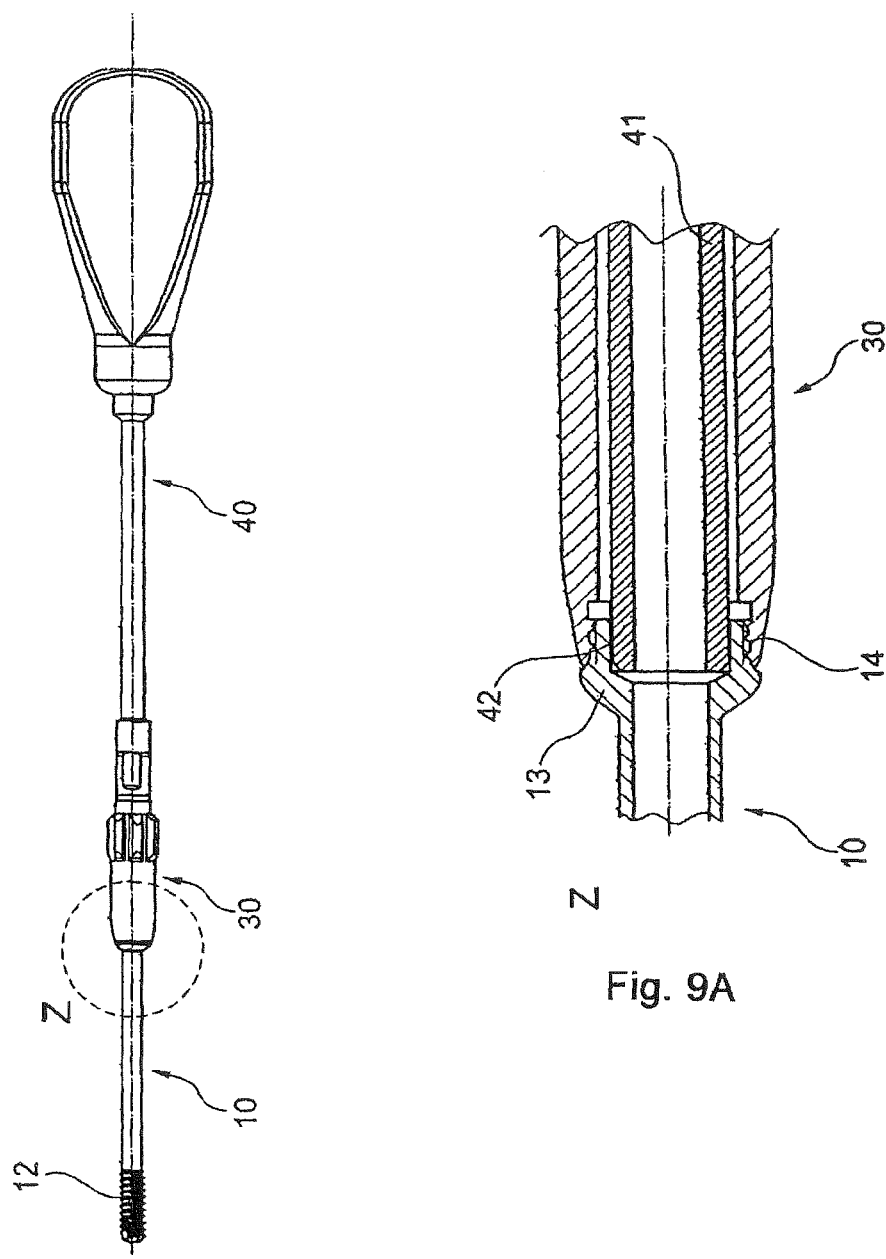
FIG. 9 is a side view and FIG. 9A is an enlarged section view of an assembled set for installation of a screw according to the invention.

FIGS. 9 and 9A, an assembly of screw 10, tissue protection sleeve 30 and a screw driver 40 is shown. Furthermore, the detail view Z in FIG. 9A shows the connection portion of the three mentioned elements in section. As depict, the shaft 41 of screw driver 40 engages with its driving end 42 in the inner engagement portion of the screw, and tissue protection sleeve 30 engages with its thread at its distal end in the outer thread 14 at the proximal end of the screw. In the enlarged view of FIG. 9A it can also be seen that the outer contour of the collar 13 of the screw 10 and end portion of the sleeve 30 may be designed to have a smooth transition.

Figure 10:
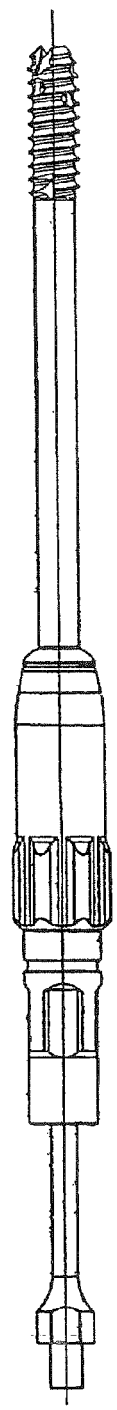
FIG. 10 is a side view and FIG. 10A is a section view of an assembled set for augmentation of a screw according to the invention.
Figure 10A:
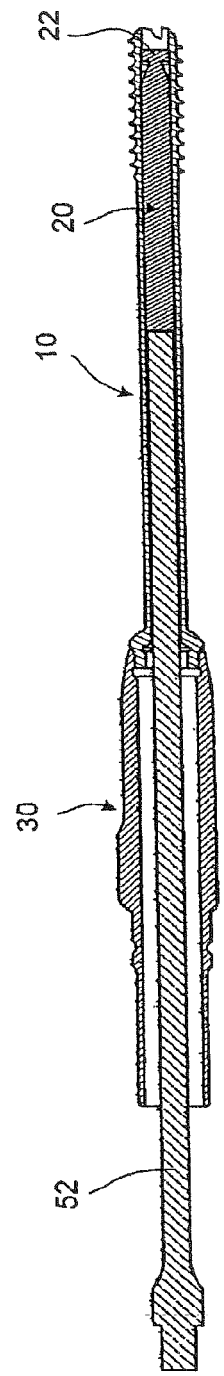

In FIGS. 10 and 10A, an assembly of screw 10, the tissue protection sleeve 30, a polymer pin 20 with an insert 22, and a sonotrode 52 of an augmentation tool like an ultrasound handpiece is shown. After removing the screw driver out of the sleeve, the polymer pin 20 may be inserted into the hollow shaft of the screw 10, through the also hollow tissue protection sleeve 30. Proximally behind the polymer pin 20 is a sonotrode inserted through the sleeve 30 and into the through bore of the screw.

It should be noted that the polymer pin 20 may also be made of other materials such as for instance a thermoplastic material suitable for augmenting a screw, both resorptive and non-resorptive materials being useful. Further, it is to be noted that the technology described with respect to an implantation of a screw into a bone, is not just limited to the indications. In other words, all screw applications which can be supplied by cannulated screws can be potentially supplied by the set and screw in accordance with the invention. Advantageously, the material into which the screw will be screwed in, is a porous material. Furthermore, the material of the so called polymer pin may have adhesive properties, especially in case of an application in a non-medical field.

While the invention has been illustrated and described in detail in the drawings and foregoing description, such illustration and description are to be considered illustrative or exemplary and. not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A sonic screw system comprising:
   a. a monolithic bone screw extending along a central longitudinal axis for implantation into a bone for fixation of a fracture, the monolithic bone screw includes a partially threaded distal shaft portion, a radially outwardly extending collar, an externally threaded proximal shaft portion, and a through bore extending along the central longitudinal axis of the monolithic bone screw through the distal shaft portion, the collar and the proximal shaft portion;

said partially threaded distal shaft portion extends along the central longitudinal axis from a distal tip of the bone screw to said radially outwardly extending collar, and said distal shaft portion having a first externally threaded portion extending along the central longitudinal axis from the tip towards the collar, and a second externally unthreaded portion extending along the central longitudinal axis from the threaded portion to the collar, said first portion has a first maximum diameter and includes a plurality of radial openings connecting the through bore with the external threads;

said radially outwardly extending collar is located on a proximal end of the distal shaft portion and having a second maximum diameter, and the collar has a distal part-spherical surface facing towards the distal tip and a proximal inwardly tapering surface facing towards the proximal shaft portion, the collar forms an annular surface between the distal shaft portion and the proximal shaft portion;

said externally threaded proximal shaft portion extending along the central longitudinal axis from the collar to a proximal end of the bone screw said proximal shaft portion is externally threaded and having a third maximum diameter, said second maximum diameter is greater than the first and third maximum diameters; and the third maximum diameter is greater than the first maximum diameter, and said proximal shaft portion includes an inner tool engagement socket at the proximal end of the bone screw having non-circular torque transmitting surface;

b. a polymer pin made of a thermoplastic fluidizable material which is fluidizable by applying ultrasound energy, said through bore includes a step adjacent the distal tip, said step has a narrower diameter than a diameter of the through bore, such that the polymer pin is seated on the step when being inserted into the through bore of the shaft;

c. a driving tool having a driving tip shaped to engage with the inner tool engagement socket at the proximal end of the screw;

d. a hollow tissue protection sleeve extending longitudinally from a distal end to a proximal end, said distal end of the sleeve includes an inner threaded portion, the inner threaded portion being configured to engage the external thread of the proximal shaft portion, and said proximal end of the sleeve includes a gripping portion diametrically enlarged relative to the distal end of the sleeve, such that, when engaged they form a screw-sleeve assembly with greater length than an entire length of the bone screw, the tissue protection sleeve includes a longitudinal channel extending therethrough being configured to partially accommodate the driving tool, the hollow tissue protection sleeve distal end outer surface located adjacent the annular collar surface when assembled to the screw, the sleeve distal end outer surface tapering inwardly to a diameter not greater than the second maximum diameter, and configured to abut the tapering surface of the collar;

e. an augmentation tool including a sonotrode for fluidizing the polymer pin material of the polymer pin, wherein the augmentation tool is configured to be mounted on the proximal end of the tissue protection sleeve, and the sonotrode configured to extend through the channel of the protection sleeve and in the through bore of the bone screw to and contacts a proximal end of the polymer pin when the pin is seated on the step in the through bore of the bone screw and configured to transmit an ultrasonic vibration to the polymer pin; and wherein the protection sleeve is configured to connect with the bone screw to facilitate the introduction of the driver and the sonotrode therethrough without interfering with surrounding tissue.

2. The system according to claim 1, wherein the inner tool engagement socket of the screw is formed to fit with a hexagonal or torx screw driver.

* * * * *